(12) United States Patent
Rincker et al.

(10) Patent No.: US 10,213,184 B2
(45) Date of Patent: Feb. 26, 2019

(54) ULTRASOUND HEAD FRAME FOR EMERGENCY MEDICAL SERVICES

(71) Applicant: KONINKLIJKE PHILIPS N.V., Eindhoven (NL)

(72) Inventors: Maarten Johan Frido Rincker, Eindhoven (NL); Juliana Pauline Kelly, Eindhoven (NL); Ralf Seip, Carmel, NY (US); Jeffry Earl Powers, Bainbridge Island, WA (US); William Tao Shi, Briarcliff Manor, NY (US); Helle Ullerup, Eindhoven (NL); Davy Maria Willibrordus Schaeken, Eindhoven (NL); Terrence James Sweeney, Redmond, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 660 days.

(21) Appl. No.: 14/435,539

(22) PCT Filed: Oct. 10, 2013

(86) PCT No.: PCT/IB2013/059268
§ 371 (c)(1),
(2) Date: Apr. 14, 2015

(87) PCT Pub. No.: WO2014/060914
PCT Pub. Date: Apr. 24, 2014

(65) Prior Publication Data
US 2015/0297176 A1    Oct. 22, 2015

Related U.S. Application Data

(60) Provisional application No. 61/716,007, filed on Oct. 19, 2012, provisional application No. 61/865,279, filed on Aug. 13, 2013.

(51) Int. Cl.
*A61B 8/00* (2006.01)
*A61B 8/08* (2006.01)
(Continued)

(52) U.S. Cl.
CPC .......... *A61B 8/4209* (2013.01); *A61B 8/0808* (2013.01); *A61B 8/40* (2013.01);
(Continued)

(58) Field of Classification Search
CPC ....... A61B 8/06; A61B 8/0808; A61B 8/0816; A61B 8/40; A61B 8/4209; A61B 8/429;
(Continued)

(56) References Cited

U.S. PATENT DOCUMENTS

| 5,334,133 A | 8/1994 | Carroll |
| 2005/0027222 A1 | 2/2005 | Harty |

(Continued)

FOREIGN PATENT DOCUMENTS

| JP | H10258064 A | 9/1998 |
| JP | 2006305047 A | 11/2006 |

(Continued)

*Primary Examiner* — Michael T Rozanski

(57) ABSTRACT

A head frame for a medical patient includes support for a probe and a neck support. The frame wraps around the head of the patient and can be used in the supine position. The support may include a probe holder slidable under the head and configured to contact or engage the neck support. In some embodiments, conformal shaping to the head and/or neck of the patient, the frame's rigid construction, the alignment of the optionally separable holder to the neck support, the weight of the head, or a combination thereof serve to keep the distal tip of the ultrasound probe in place against the temporal region of the head without need for attaching the frame to the head as by straps, which may provide an arrangement robust against patient/vehicle movement in an emergency medical services setting.

17 Claims, 4 Drawing Sheets

(51) Int. Cl.
   *A61G 1/04*   (2006.01)
   *A61N 7/00*   (2006.01)
   *A61B 8/06*   (2006.01)
   *A61B 90/14*  (2016.01)

(52) U.S. Cl.
   CPC ............ *A61B 8/429* (2013.01); *A61B 8/4427* (2013.01); *A61G 1/04* (2013.01); *A61N 7/00* (2013.01); *A61B 8/06* (2013.01); *A61B 8/0816* (2013.01); *A61B 8/4411* (2013.01); *A61B 8/4455* (2013.01); *A61B 90/14* (2016.02); *A61N 2007/0021* (2013.01); *A61N 2007/0026* (2013.01); *A61N 2007/0039* (2013.01); *A61N 2007/0052* (2013.01)

(58) Field of Classification Search
   CPC ... A61B 8/4411; A61B 8/4427; A61B 8/4455; A61B 90/14; A61G 1/04; A61N 2007/0021; A61N 2007/0026; A61N 2007/0039; A61N 2007/0052; A61N 7/00
   See application file for complete search history.

(56)         References Cited

U.S. PATENT DOCUMENTS

| | | |
|---|---|---|
| 2007/0151390 A1 | 7/2007  | Blumenkranz |
| 2010/0160779 A1 | 6/2010  | Browning |
| 2010/0222723 A1 | 9/2010  | Hoffmann |
| 2011/0251489 A1 | 10/2011 | Zhang |
| 2012/0165670 A1 | 6/2012  | Shi |

FOREIGN PATENT DOCUMENTS

| | | |
|---|---|---|
| WO | 2007044469 A2 | 4/2007 |
| WO | 2010042146 A2 | 4/2010 |
| WO | 2014207665 A2 | 12/2014 |

ULTRASOUND HEAD FRAME FOR EMERGENCY MEDICAL SERVICES

CROSS-REFERENCE TO PRIOR APPLICATIONS

This application is the U.S. National Phase application under 35 U.S.C. § 371 of International Application No. PCT/IB2013/059268, filed on Oct. 10, 2013, which claims the benefit of U.S. Provisional Patent Application No. 61/716,007, filed on Oct. 19, 2012 and U.S. Provisional Patent Application No. 61/865,279, filed on Aug. 13, 2013. These applications are hereby incorporated by reference herein.

FIELD OF THE INVENTION

The present invention relates to a head frame for supporting a probe for imaging, therapy or both and, more particularly, to a head frame that includes neck support and wraps around the head.

BACKGROUND OF THE INVENTION

Sonothrombolysis (STL) is an emerging non-invasive stroke treatment modality in which ultrasound and microbubbles are used to lyse the clot causing the occlusion in acute ischemic strokes. In these treatments, ultrasound (used to both image/locate the occlusion in the brain vasculature and treat it), is applied via appropriate probes, typically positioned on the patients' temporal bone/window. The temporal bone provides acoustic access to the brain with the smallest amount of signal attenuation and aberration. During these treatments (which could last up to 2 hours), it is important to maintain the position and orientation of the ultrasound probes fixed and directed at the occlusion location for best treatment. Probes are typically held in place against the patients' temporal bone via a headset.

STL uses ultrasound targeting the clot, microbubbles (in systemic circulation), and sometimes a thrombolytic drug such as t-PA (tissue plasminogen activator, a "clot-busting" agent), to break up the fibrin structures that make up a typical clot, so as to try to restore normal blood flow to the occluded region in the brain. Currently, clinical trials are ongoing in sonothrombolysis, using either a combination of (i) ultrasound and t-PA or (ii) ultrasound, t-PA, and microbubbles.

Such treatments typically use head-mounted, single-element transducer(s)/probes to deliver the ultrasound through the temporal bone, operate in continuous or pulsed mode, and typically do not have the ability to target the ultrasound beam, other than using manual positioning of the ultrasound probes mounted in a headframe. The ability to more precisely orient the beam toward a blood clot is overcome by placing many single-element probes on the patients skull, with the expectation that at least one of the beams is aligned and targeting the clot.

Commonly-assigned United States Patent Application No. 2010/0160779 to Browning et al. features a conventional safety helmet for blood clot lysis. The helmet is configured for keeping a pair of ultrasound probes in contact with the temporal regions of both sides of the head. A liner inside the helmet wraps around a circumference of the head. With the probes positioned inside the liner, the liner functions as a transcranial headset. The probes have matrix arrays usable for electronic steering. The probes are utilizable for imaging or therapy, including imaging guidance for steering a therapy beam. Once it is seen, via the imaging guidance, that the probes are suitably positioned, the helmet liner headset can be adjustably secured in place by an adjustment knob.

SUMMARY OF THE INVENTION

What is proposed herein below is directed to addressing one or more of the above-discussed concerns and to further improvements.

Current head frames (or headbands) are designed to be used in a clinic, stroke center, and/or emergency department. Most designs follow the headband approach, with patients typically in sitting position during usage, where the probe/head registration is implemented mostly by fixing the band to the patient's head.

While comfortable, it is unlikely that such head frames would withstand the rigors of maintaining accurate probe alignment and targeting to the clot in an emergency vehicle, where the patient and his/her head is constantly in motion because of the motion of the emergency vehicle itself.

In particular, most current head frames or headbands use the head as the only attachment and reference point for holding the probe to it, i.e., the probe is attached to a headpiece that is then attached to the patient's head.

This may be advantageous in an emergency room (ER)/hospital setting, but may not be the best solution in an emergency medical services (EMS) setting.

It is important to start STL as early as possible after the stroke diagnosis (i.e., in a point-of-care setting), and continue the treatment while the patient is being transported to a treatment center, as "time is brain."

Also, the "blind therapy" approach of providing multiple therapy beams with the intention of one or more being aimed at the blood clot has the unintended side effect that healthy brain tissue is treated unnecessarily.

An STL head frame, according to embodiments of what is proposed below, is designed specifically to meet the requirements for holding the probes against a patients' head for robust probe placement, for quick application by EMS personnel and for providing STL therapy during patient transport to the treatment center, compatible with current EMS workflow.

The novel approach also involves aligning and orienting the ultrasound therapy beam under ultrasound image guidance. Ultrasound images can be used to locate the position of the clot/occlusion within the brain, and can thus be used to direct the ultrasound therapy beam to this same location. In some cases, the ultrasound imaging probe can also be used for the STL therapy, in a dual-mode arrangement. In other cases, a separate ultrasound imaging probe and therapy probe can be used in this image-guided therapy. This scenario subjects only the area of the brain that requires it (i.e., the region containing the occlusion) to the therapeutic ultrasound energy. This reduces the overall ultrasonic dose, and further allows monitoring of the progress of the treatment via the imaging ultrasound, to, for example, stop the treatment once vessel recanalization has been detected. For this approach to work in practice, however, and more importantly in an EMS setting, both the imaging and therapy probe(s) are to be held steadily and tightly coupled to the patients head for the duration of the treatment (in the case of separate probes being used for occlusion imaging and occlusion therapy), or the single, dual-purpose imaging/therapy probe is to be held steadily and tightly coupled to the patients head (in the case of a dual-use probe).

Such coupling and alignment should be robust, stable, resist vibrations, resist patient/probe relative motion, be comfortable, and easily applied to the patient. It should allow for probe coupling for the entire duration of the STL treatment, even during patient transport. Stroke treatment outcomes are generally better the earlier a patient is treated for the stroke ("time is brain"). Thus treatment at the point-of-care site and during transport is highly desirable. Currently, stroke patients are not treated for stroke until after arrival at a hospital and/or stroke unit, wasting valuable time (and brain).

In accordance with an aspect of what is proposed herein, a head frame for a head of a medical patient includes a neck support and support for a probe configured for imaging, therapy, or both imaging and therapy. The frame has a configuration that wraps around the head.

As a sub-aspect, an imaging apparatus includes the head frame and a motorized assembly for positioning of the probe on a temporal bone window of the head. The apparatus is configured for, automatically and without need for user intervention, performing the positioning under closed-loop imaging guidance afforded via the probe.

Alternatively or in addition, the head frame includes a device configured for measuring force by which the frame applies the probe to the head. Also, responsive to the measurement, the device performs user notification and/or adjustment of the force.

In complementary, related versions, for the immediately-above-mentioned imaging apparatus and/or the force measuring device, a computer readable medium or alternatively a transitory, propagating signal is part of what is proposed herein.

Details of the probe holding and positioning technology for supine cranial patients are set forth further below, with the aid of the following drawings, which are not drawn to scale, and in which the reference numerals pertain to the same or similar structures throughout the several views.

DETAILED DESCRIPTION OF EMBODIMENTS

Figure 1A:
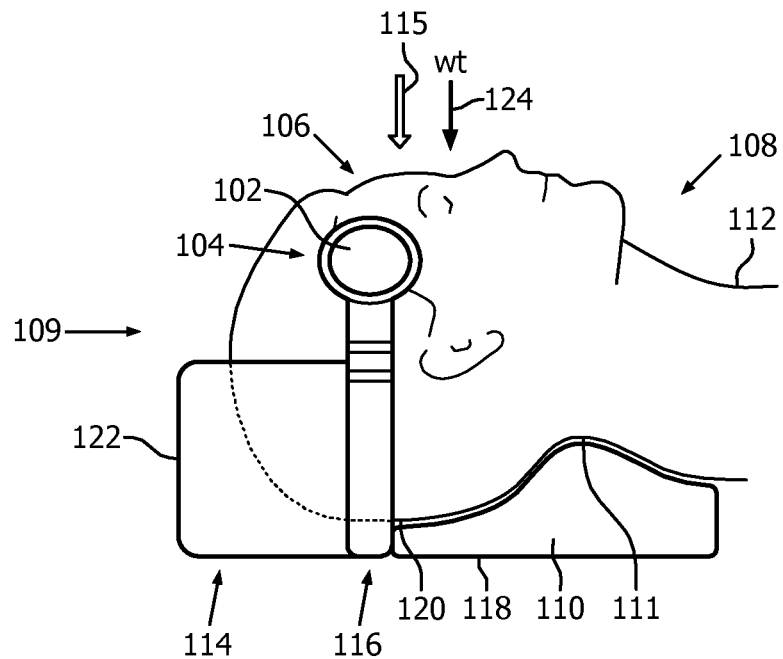
FIGS. 1A and 1B are schematic diagrams of front views of exemplary, respective EMS head frames in accordance with the present invention.

FIG. 1A depicts, by way of illustrative and non-limitative example, an integrated head frame 100. It has a circular opening 102 for holding an imaging probe (or a therapy probe, or a combined imaging/therapy probe, not shown) such as one used for ultrasound imaging. The distal tip of the probe is placed against a temple, or temporal bone region, 104 of a head 106 of a medical patient 108. Located within the temporal bone region 104 is the acoustic window in the skull with minimum acoustic attenuation. The head frame 100 is specifically designed for use for an EMS patient 108 in the supine position 109, i.e., lying down facing upward. Although basic components of the head frame 100 may be integrated or not normally separable, parts of the head frame may be made detachable for cleaning or replacement.

The head frame 100 includes a neck support 110 conformal with the back 111 of the neck 112, and has a configuration 113 that wraps around the head 106.

In particular, the head frame 100 further includes support 114 for the ultrasound probe in the form of a probe holder 116 that has, at its upward end, the above-mentioned circular opening 102. Another upstanding structure (not shown) of the probe holder, that structure containing another circular opening, projects upward on the other side of the head 106 and is usable to support another probe (not shown). In either case, i.e., one or two upstanding structures, the configuration 113 wraps around the head 106. This includes the back of the head, and one or two sides. Integral with the conformal neck support 110, is a conformal support or base 118 for conformal placement against the back 120 of the head 106. The back-of-the-head support 118 includes an upstanding, conformal outer rim 122. Both extend upward to surround an upper part of the back 120 of the head 106. In particular, the base 118 and/or the neck support 110 are shaped conformally with the back of correspondingly the head 106 and/or the neck 112. Notably, the holder 116 is not configured for attachment to the head 106. Instead, weight 124 of the head 106 serves, via the probe support 114, to keep the probe in place against the head 106. Likewise, the conformality serves to keep the probe in place against the head 106. Once the patient 108 has laid his or her head 106 down, as represented by the down arrow 115, into the head frame 100, the probe can be (further) adjusted manually or by motorized movement (as discussed further below) into registration with the temporal bone region 104. The head frame 100 allows XY adjustment of the probes by moving the probe holder up/down and left/right. Vertical motion is provided by a vertical slot 126, and adjustable as indicated by the slack in between an upper guide 128 and a lower guide 130. A horizontal slot for left/right movement is provided by a track (not shown) in the form of a horizontal slot into which the probe holder 116 fits. Both slots provide a rigid, friction fit. Alternatively or in addition to the horizontal slot, a vertical slot may be provided in the rim 122. Probe rotation and angulation is accomplished by fixing the probe within a spherical structure that is mounted and fixable within the circular opening 102. The circular opening 102 has an inside surface that is shaped like a section of a sphere. The spherical structure may be a pair of mating clam-shell shaped pieces. The outside of the mated pieces forms a matching spherical surface, and the inner surface of the mated pieces matches the periphery of the particular type of probe being held. The two pieces together constitute a probe adaptor that is loosely held within the opening 102 for angulation. A clamping mechanism such as an expandable, outer, friction surface of the adaptor operable by a user-accessible lever fixes the adapter in place. Other, alternative mechanisms may be employed. For instance, the circular opening 102 can be interrupted and therefore expandable, and compressible by means of a user-adjustable clamp. "Z" positioning can be afforded by a friction slot surrounding and concentric with the circular opening 102. A number of probe positioning schemes for a head frame are presented in the commonly-assigned provisional filing 61/716,007 entitled "Ultrasound Headset Design and 61/865,279 entitled "Ultrasound Head Frame for Emergency Medical Services" the entire disclosures of which are incorporated herein by reference. As an alternative discussed below, X-Y-Z positioning (along three orthogonal axes), as well as rotation/angulation, are implementable with a motorized embodiment. The registration of the distal tip of the probe to an acoustic window of the temporal bone region 104 is maintained by the rigid construction of the head frame 100, the weight of the head 106 and the conformality. In this arrangement, the head frame 100 does not impede the placement of other items on the patient's face and/or head, such as a face mask for oxygen flow. This is consistent with the EMS workflow for patient stabilization, readying for transport via a transport stretcher, and transport in the EMS vehicle such as an ambulance or helicopter. The head frame 100 may include an attachment mechanism for firm attachment to the underlying transport stretcher, to avoid using straps for example. The dimensions of the attachment would be compatible with those of the stretcher.

Figure 1B:
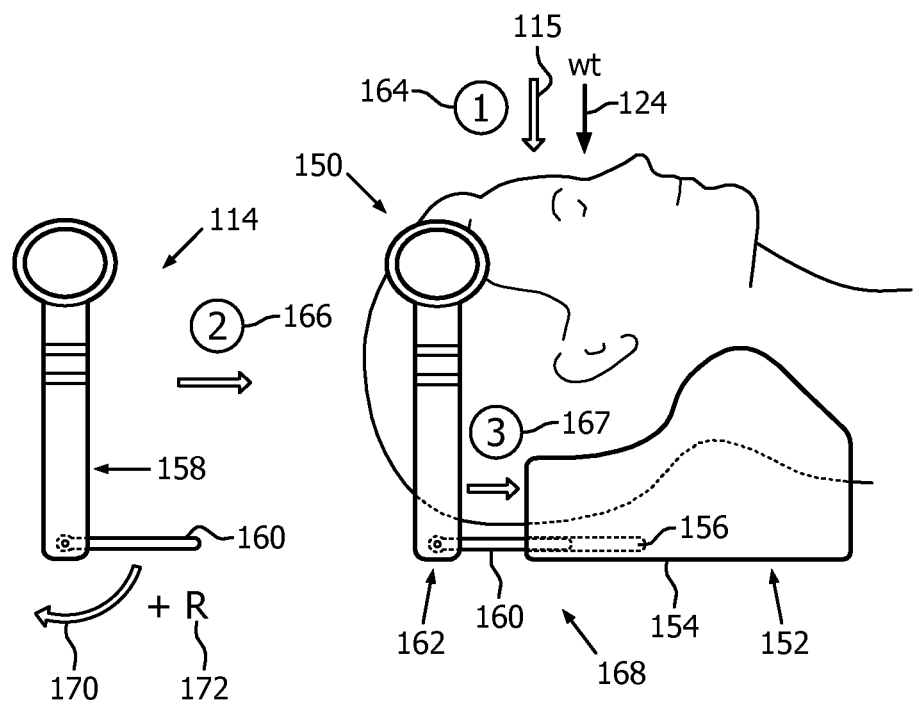

A frictional assembly based head frame 150 is shown in FIG. 1B. It includes a first, separate structure implemented as a conformal neck support 152, which includes a partial, conformal head-support 154 having a horizontal assembly slot 156. A releasably attachable probe holder 158 includes an extension 160 that fits securely, as by friction, within the slot 156. The extension 160, though it may be selectively rotatable into a reverse orientation as discussed below, is fixed, as by locking, in place to provide a fixed alignment 162 of the extension to the neck support 152. The patient 108 first, as represented by the circled number one 164, places his or her head 106 down onto the neck support 152, including the head support portion. Then, as represented by the circled number two 166, the probe holder 158 is slid toward the head support 154, inserting the extension 160 into the slot 156 to thereby contact the neck support 152. On the right, the extension 160 is shown partially inserted. To fully engage the head support 154 and bring the circular opening 102 over the temporal bone region 104, the extension 160 is slid fully into the slot 156, as represented by the circled number three 167. In this embodiment, the probe holder 158 is slid into releasable, frictional engagement with the neck support 152 by means of the extension 160 and the slot 156. The design of the head frame 100 is such that the insertion forms a second structure 168, i.e., the head frame itself, down into which the head 106 (though already in place) is placeable. The alignment 162, the conformality, and the weight 124 of the head 106 keep the probe, via the probe holder 158, in place. "X" positioning is achieved by adjusting the extent of insertion of the extension 160, and "Y" positioning is achieved via the same vertical slot configuration as in FIG. 1A that includes the upper and lower guides 128, 130. "Z" positioning, and probe rotation/angulation are also implementable in the same manner described above with regard to FIG. 1A. As with the integrated head frame 100 of FIG. 1A, the probe holder 158 includes another upstanding structure on the other side for another probe that contacts the other temple of the patient 108. As mentioned above, the extension 160 is rotatable 170 by 180° into a reverse orientation 172. The extension 160 can then be locked into place, as by in-plane spring-loaded buttons having a rounded exterior for urging them in at the end of the rotation. The buttons are withdrawable by a user control to release the lock. This allows attached probes to be reversed on the head 106 without probe interchange. Since one probe may be specialized for therapy with the other specialized for imaging, flexibility in treating a number of patients in increased with deployment time being reduced. Also, for the designs described above with regard to FIG. 1*a*, here too, defective probes may be quickly removed or replaced.

Figure 2A:
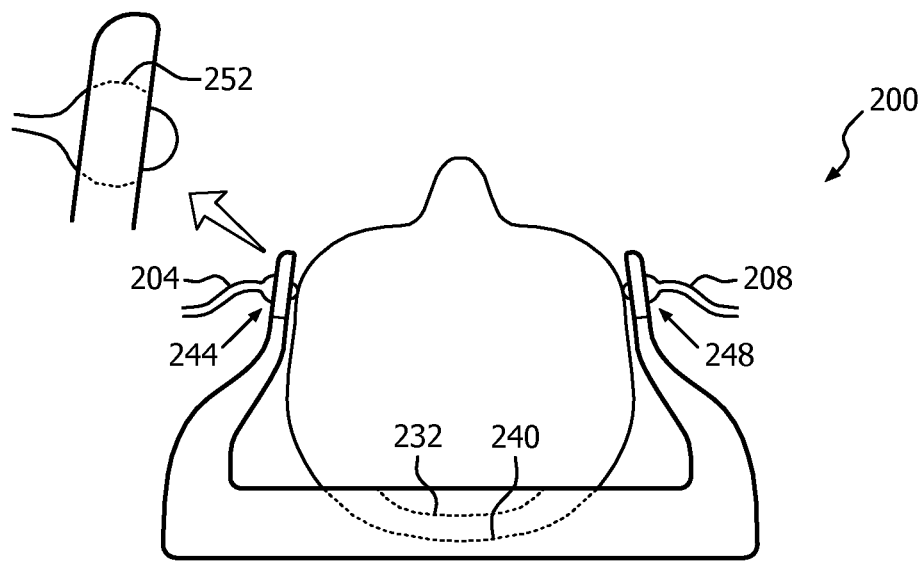
FIGS. 2A and 2B are respective schematic diagrams of a side, and top, view of an exemplary EMS head frame in accordance with the present invention.
Figure 2B:
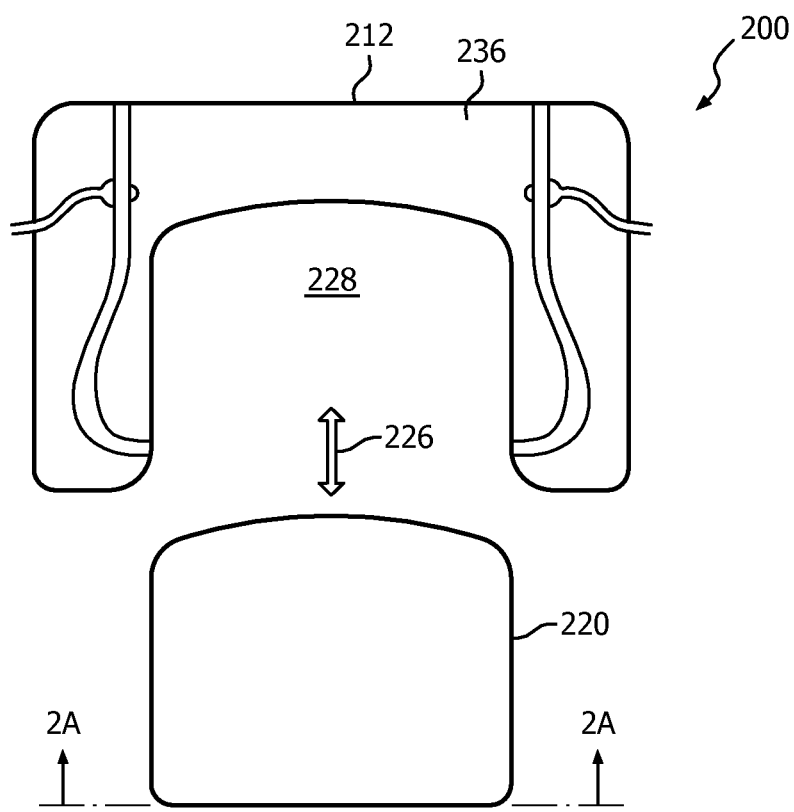

The slot based friction is optional. A sliding assembly head frame 200, shown by example in FIGS. 2A and 2B, relies on conformality, the weight 124 of the head 106, and the rigid construction for keeping probe(s) 204, 208, via a probe holder 212, in place against the temporal bone region 104 of the head 106. The head frame 200 includes, as best seen in FIG. 2B, a U-shaped neck support 220, and the probe holder 212 has a matching U-shaped indentation 228 or cut-out. The neck support 220 need not be configured attached or releasably attachable to the probe holder 212; instead, with the head 106 resting on the neck support, the probe holder may be slid 226 into, or out of, adjacency or contact with the neck support. The neck support 220 has a top surface that is conformally shaped to the back 111 of the neck 112, as represented by the broken line 232. Similarly, the probe holder 212 has a base 236, for receiving the head 106 in a supine position, whose top surface is conformally shaped to the back 120 of the head 106, as represented by the broken line 240. Part of the conformal shaping of the neck support 220 may also be to the back 120 of the head 106. So, the base 236 is conformally shaped to the back 120 of the head 106, and the neck support 220 is, at least in part, shaped conformally with the back 111 of the neck 112. The neck support 220 may be adjustable in that it need not be inserted all to way into the U-shaped indentation 228. The probe holder 212 has openings 244, 248 for holding the probe(s) 204, 208. The left-side opening 244 is shown, by the exploded view in FIG. 2A, to have a spherical cross-section 252, as discussed above with regard to the embodiment of FIG. 1A. The same applies to a right-side opening (not shown). In particular, mirror-image symmetry of the head frame, with respect to both sides of the head 106, applies to all of the embodiments within this patent application.

Figure 3:
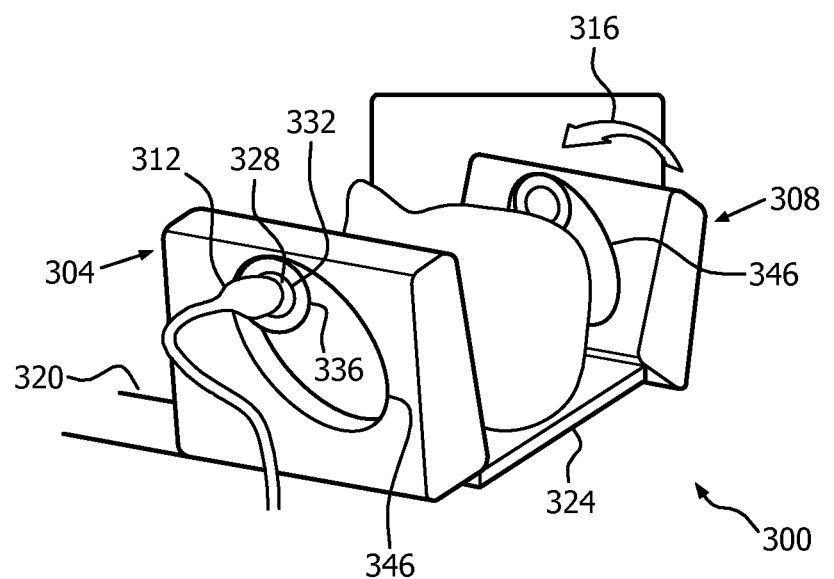
FIG. 3 includes a perspective view of an exemplary EMS head frame, and top views of versions of an immobilizing member of the exemplary EMS head frame, in accordance with the present invention.
Figure 3:
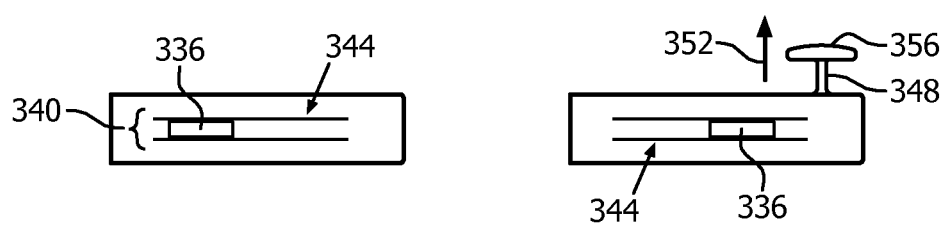

FIG. 3 is one possible realization of a folding head frame 300. Ultrasound probe support is provided by immobilizing members 304, 308 configured for being angled away to take their respective probes 312 out of engagement with the head 106, and for being angled back 316 to re-establish the engagement. An angled back immobilizing member 304 serves to keep its probe 312 rigidly in place against the head 106. The head frame 300 may further include hinges (not shown) for the angling away and back. The hinges are attachable to a transport stretcher 320, making straps for securing the head 106 unnecessary. Other attaching hardware may include screws, square brackets with screw holes, and threaded receptacles on the sides of the stretcher 320 and underneath the base 324. The probe 312 is surrounded and held by an adaptor 328 that is insertable into a circular opening 332 of a plate 336 which may be made of metal or hard plastic. The opening 332, as in the previous-described embodiments, has a spherical cross-section matching an outer surface of the adaptor 328. The plate 336 is sandwiched 340 by two opposing surfaces that define a slot 344 within the immobilizing member 304. The plate 336 is disposed in sliding engagement with the member 304, 308, the folding head frame 300 being configured for sliding the plate in relation to the member to position the probe 312. The lateral dimensions of the plate 336 are large enough so that, no matter where the plate 336 is slid within the slot 344, the opening 332 is fully accessible to the user by means of an orifice 346 in the immobilizing member 304. Through the orifice 346, contact of the probe 312 with an acoustic window of the temporal bone region 104 is achievable. User-turnable knobs (not shown) on the outside of the immobilizing member 304 may be used to secure the plate 336 in place once the desired or targeted X-Y positioning is achieved. "Z" positioning may be achieved by means of the concentric friction slot described for the first embodiment above. Alternatively, the positionings may be motorized, as described in more detail below. The immobilizing member 304 may optionally be supplemented with a skull stabilizer 348 configured for, from the standpoint of the member being in the angled back position, projecting inward, as represented by the arrow 352, to contact the head 106 so as to stabilize the head. The skull stabilizer 348 has a pad 356 at its distal end where it contacts the patient 108. Here again, mirror-image symmetry may be implemented with respect to the configuration of the head frame 300 on both sides of the head 106.

The folding head frame 300 offers easy probe positioning and adjustment, because the probe mounting structures, i.e., immobilizing members 304, 308 can be folded or angled away from the patient's head 106 without having to re-position the patient on the transport stretcher 320. This, for example, is not easily implementable with the current designs which use headbands to hold the probe against the patient's head. The fold away feature offers application of ultrasound gel during the treatment should the acoustic coupling have diminished over time, without having to re-position or re-target the probe when the immobilizing member 308 is angled back 316. The same applies to those instances when acoustic coupling pads are to be applied in place of gel such as when additional probe angulation is required that a gel coupling may not provide reliably. The overall form factor, access to the patient, and the ability to hold probes firmly during transport are all advantages of the folding head frame 300.

Figure 4:
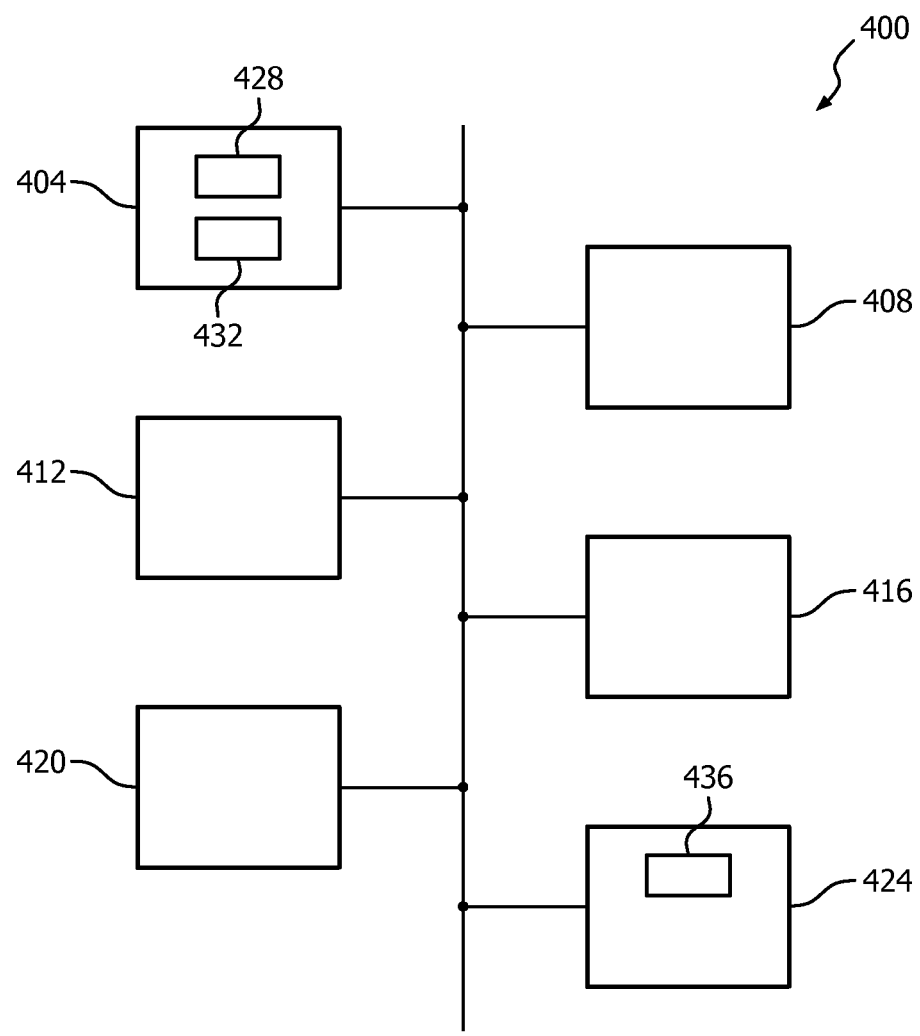
FIG. 4 is an example of an automatic probe positioning system in accordance with the present invention.

An automatic probe positioning system 400, an example of which is seen in FIG. 4, includes ultrasound probes 404, an X-Y-Z motorized assembly 408 for positioning the probes along three orthogonal axes, an ultrasound scanning processor 412, an ultrasound transcranial aberration correction processor 416, a user interface 420, and a microcontroller 424.

The probes 404 each include strain gauges 428, and wireless communication circuitry 432 for transmitting readings from the strain gauges. The microcontroller 424 also has wireless communication circuitry 436 for receiving the readings. Alternatively, a wireline embodiment can communicate with the microcontroller 424 via the cable. The strain gauges 428 may be provided longitudinally in an axial direction of the probe 404, within the housing shallow beneath the surface, arranged spaced apart circumferentially around the probe, and disposed near the distal tip of the probe, i.e., between the adaptor and the patient 108. An example of a similar strain gauge configuration is provided in FIGS. 2 through 7 of United States Patent Publication No. 2007/0151390 to Blumenkranz et al., the entire disclosure of which is incorporated herein by reference. Similar configurations of the gauges 428 can be incorporated also or instead into the probe holders or probe adaptors. The axial strain readings of the gauges 428 are usable by the microcontroller 424 in making, responsive to the readings, small comfort adjustments during treatment without losing acoustic coupling to the temporal bone. The adjustments made, via the motorized assembly 408, are to the force the distal tip of the probe 404 applies against the patient 108. Alternatively or in addition, the measured force is reportable to the clinician by output capabilities of the user interface 420, such as by display on a monitor. Detection that the probe 404 is no longer in contact with the patient's head 106 can alternatively be afforded by the force feedback, along with user notification and optionally automated corrective adjustment.

The motorized assembly 408 can perform the X-Y-Z translations for positioning of a probe 404 on a temporal bone window of a head 106, automatically and without the need for user intervention, under closed-loop imaging guidance afforded via the probe(s) 404. For instance, the ultrasound transcranial aberration correction processor 416 is invoked to determine device settings, as described in commonly-assigned United States Patent Publication No. 2012/0165670 to Shi et al., (hereinafter "the Shi application"), the entire disclosure of which is incorporated herein by reference. One type of device setting to be adjusted to attain an optimal acoustic window is the transmit and/or receive aperture of the ultrasound transducer(s) in the probe(s) 404. Another type is the X-Y location of the transducer, such as a matrix array transducer. The translation can be done in real time under the closed-loop image guidance afforded via the probe(s) 404. "Z" positionings are also made optionally in real time by the motorized assembly 408 in, for example, comfort adjustments as described above, and by means of the concentric slot translations described herein above. Probe rotation/angulation can likewise be motorized to assist in finding the optimal acoustic window. Other types of automatable probe positionings include ones for inter-probe registration, as in the case where one of the probes 404 is specialized for or devoted to therapy, while the other probe is specialized for or devoted to imaging, and the therapy beam is placed under image guidance feedback. This kind of automated registration, which may be updated periodically during treatment, is discussed in the commonly-assigned US patent application Ser. No. 14/901,293 entitled "Transducer Placement and Registration for Image-Guided Sonothrombolysis", the entire disclosure of which is incorporated herein by reference. The automated positioning may also be utilizable in automated Doppler based blood flow analyses, automated stroke diagnosis, automated clot localization, automated therapeutic beam intensity monitoring, and other time and brain saving measures.

What is proposed herein above is usable in stroke therapies, especially in a point-of-care setting or EMS setting. Although STL is one of these therapies, application extends also to diagnostic uses of ultrasound in brain applications, including trans-cranial color Doppler (TCD) examinations with ultrasound. Because of its steady design, the head frame may be employed in intensive care unit (ICU) continuous monitoring. This would include ICU monitoring with updates every 5 to 30 minutes, as applied to cerebral anatomy and blood flow conditions of critically ill patients who are not movable for access to computed tomography (CT), or are unwilling to be continuously exposed to the ionizing CT. Additional applications are those that involve ultrasound/microbubble combination for therapy purposes, including applications for the treatment of mild traumatic brain injury (mTBI) and blast-induced traumatic brain injury (bTBI).

Although presented above in the context of ultrasound imaging and probe placement, what is proposed herein extends to any type of medical imaging, e.g., photoacoustic, infrared, optical, for which one or two probes are to be maintained in fixed contact with the head of a patient.

A head frame is configured for the head of a medical patient and includes support for a probe and a neck support. The frame wraps around said head, and can be used in the supine position. The support may include a probe holder slidable under the head and to contact or engage the neck support. In some embodiments, conformal shaping to the head and/or neck, the frame's rigid construction, the alignment of the optionally separable holder to the neck support, and weight of the head all serve to keep the distal tip of the ultrasound probe in place against the temporal region of the head, without need for attaching the frame to the head as by straps, providing an arrangement robust against patient/ vehicle movement in an emergency medical services setting. Head immobilizing walls may be folded away in some versions, retaining probe alignment. In the holder, an optional circular opening with a spherical cross-section allows the probe(s) to be rotated into position, and X-Y-Z positioning too may be provided, all manually or by motor.

While the invention has been illustrated and described in detail in the drawings and foregoing description, such illustration and description are to be considered illustrative or exemplary and not restrictive; the invention is not limited to the disclosed embodiments.

For example, within the intended scope of what is proposed herein is a computer readable medium, as described below, such as an integrated circuit that embodies a computer program having instructions executable for performing the probe application strain monitoring and adjustment and the motorized probe positioning. The functions are implementable by any combination of software, hardware and firmware. Also, the term "medical patient" pertains to human beings, and to animals that are anesthetized and are subject to brain diagnosis or therapy. In addition, a thin layer of cushioning may be provided where the head frame contacts the patient.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as a floppy disk, a magnetic hard disk drive, a solid-state medium such as a solid state hard disk, flash memory, a USB thumb drive, read-only memory (ROM), an optical storage medium such as an optical disk, and a magneto-optical disk. Examples of optical disks include compact disks (CD) and digital versatile disks (DVD), for example CD-ROM, CD-RW, CD-R, DVD-ROM, DVD-RW, or DVD-R disks. Such a computer-readable medium is non-transitory only in the sense of not being a transitory, propagating signal, but includes other forms of computer-readable media such as register memory, processor cache, RAM and other volatile memory.

A single processor or other unit may fulfill the functions of several items recited in the claims. The mere fact that certain measures are recited in mutually different dependent claims does not indicate that a combination of these measures cannot be used to advantage.

What is claimed is:

1. A head frame configured for a head of a medical patient, the head frame comprising:
   a probe support for a probe configured for imaging, therapy, or both imaging and therapy, wherein the probe support comprises a holder for the probe, wherein the probe support is configured to maintain the probe against the head of the patient in response to a weight of the head resting on the head frame without attaching the holder to the head of the patient; and
   a neck support of rigid construction, wherein the neck support is configured to at least partially contact and support a neck of the patient,
   wherein the probe support includes a first opening at a first upper end of a first upstanding structure for holding a first probe on a first side of the head and a second opening at a second upper end of a second upstanding structure for holding a second probe on an opposite side of the head,
   wherein the probe support has a configuration that wraps around a back of the head of the patient between the first upstanding structure and the second upstanding structure, and wherein the neck support is attachable to and separable from the probe support.

2. The head frame of claim 1, wherein the first and second openings each include an inside surface that is shaped like a section of a sphere.

3. The head frame of claim 1, wherein the neck support includes a slot, and the holder includes an extension slidable into the slot for aligning the probe support to the neck support.

4. The head frame of claim 3, wherein the holder is configured for selectively reversing a direction of the extension.

5. The head frame of claim 1, comprising a base configured for receiving said head in the supine position, said neck support entailing underlying support for said neck.

6. The head frame of claim 1, wherein the first and second openings are circular openings.

7. The head frame of claim 1, wherein the holder is configured for sliding engagement with a first structure to form a second structure into which the head is placeable.

8. The head frame of claim 1, being of rigid construction so as to maintain registration between said probe and an acoustic window of a temporal bone region of said head.

9. The head frame of claim 1, configured for attachment to a transport stretcher.

10. The head frame of claim 1, further comprising a conformal support provided, at least in part, by the holder, the neck support, an outer rim, or a combination thereof, the conformal support configured for placement conformally against a back of the head such that the weight of the head against the conformal support aids in maintaining the probe in place against the head.

11. The head frame of claim 1, wherein the probe support comprises an immobilizing wall configured to be angled away to position the probe out of contact with the head, and to be angled back to re-position the probe in contact with the head.

12. The head frame of claim 11, wherein the immobilizing wall comprises an orifice for positioning the probe in contact with an acoustic window of a temporal bone region of the head.

13. The head frame of claim 12, further comprising, alongside the orifice, a skull stabilizer projecting inward towards the head of the patient.

14. The head frame of claim 11, further comprising a plate in sliding engagement with the immobilizing wall, the plate having an opening for the probe, wherein the frame is configured for sliding the plate in relation to the immobilizing wall to position the probe.

15. The head frame of claim 1, configured for mirror-image symmetry, of said frame, with respect to both sides of said head.

16. An imaging apparatus comprising the head frame of claim 1 and a motorized assembly for positioning the probe on a temporal bone window of the head, the apparatus being configured for, automatically and without need for user intervention, performing the positioning under closed-loop imaging guidance provided by the probe.

17. The head frame of claim 1, further comprising a sensor arranged to measure a force applied to the head of the patient by the frame, and wherein the frame is further configured, responsive to the measured force, to perform at least one of user notification and an adjustment of the force.

* * * * *